(12) United States Patent
Unal et al.

(10) Patent No.: US 12,150,762 B2
(45) Date of Patent: Nov. 26, 2024

(54) BLOOD COLLECTION DEVICE

(71) Applicant: MACO PHARMA, Mouvaux (FR)

(72) Inventors: Hervé Unal, La Salvetat-Belmontet (FR); Nicolas Coasne, Radinghem en Weppes (FR); Arnaud Chavatte, Saint Floris (FR)

(73) Assignee: MACO PHARMA, Mouvaux (FR)

( * ) Notice: Subject to any disclaimer, the term of this patent is extended or adjusted under 35 U.S.C. 154(b) by 644 days.

(21) Appl. No.: 17/602,360

(22) PCT Filed: Apr. 7, 2020

(86) PCT No.: PCT/EP2020/059902
§ 371 (c)(1),
(2) Date: Oct. 8, 2021

(87) PCT Pub. No.: WO2020/208023
PCT Pub. Date: Oct. 15, 2020

(65) Prior Publication Data
US 2022/0167890 A1      Jun. 2, 2022

(30) Foreign Application Priority Data

Apr. 8, 2019 (FR) ...................................... 1903739

(51) Int. Cl.
*A61B 5/15* (2006.01)
*A61B 5/157* (2006.01)
*A61M 1/02* (2006.01)

(52) U.S. Cl.
CPC .... *A61B 5/15003* (2013.01); *A61B 5/150366* (2013.01); *A61B 5/150946* (2013.01); *A61B 5/157* (2013.01); *A61M 1/024* (2013.01)

(58) Field of Classification Search
CPC .......... A61B 5/150022; A61B 5/15003; A61B 5/150038; A61B 5/150045;
(Continued)

(56) References Cited

U.S. PATENT DOCUMENTS

| 2,784,932 A | 3/1957 | Sodetem |
| 3,960,224 A | 6/1976 | Silvers |

(Continued)

FOREIGN PATENT DOCUMENTS

| FR | 2511147 A1 | 2/1983 |
| WO | 2016084001 A1 | 6/2016 |
| WO | 2017216343 A1 | 12/2017 |

OTHER PUBLICATIONS

International Search Report issued in corresponding application No. PCT/EP2020/059902 dated May 18, 2020.

*Primary Examiner* — Eric F Winakur
*Assistant Examiner* — Abel Seifu Abegaz
(74) *Attorney, Agent, or Firm* — Murtha Cullina, LLP (57) ABSTRACT

The inventive apparatus is a device for collecting a target volume of blood in a collecting bag connected to a collection needle with a flexible tube. The device has a plate for the collecting bag and a clamping device for clamping the flexible tube. The device also has a bearing element having a bearing surface, and a clamping element with a clamping surface. The clamping element is able to move between an open position in which the flexible tube positioned between the bearing and clamping surfaces is not deformed and a closed position in which the flexible tube positioned between the bearing and clamping surfaces is closed off. The device also has a control unit configured to determine the volume of blood collected and move the clamping element from the open position to an intermediate position, when the determined volume of blood collected reaches a predetermined volume.

11 Claims, 5 Drawing Sheets

(58) Field of Classification Search
CPC ........ A61B 5/150366; A61B 5/150946; A61B 5/157; A61M 1/024; A61M 1/0245; A61M 1/025
See application file for complete search history.

(56) References Cited

U.S. PATENT DOCUMENTS

| | | |
|---|---|---|
| 4,678,049 A | 7/1987 | Gummere et al. |
| 4,923,449 A | 5/1990 | Toya et al. |
| 2012/0265099 A1 | 10/2012 | Goodnow, II et al. |
| 2019/0143012 A1* | 5/2019 | Sala .................... A61M 1/0245 604/254 |

* cited by examiner

BLOOD COLLECTION DEVICE

CROSS REFERENCE TO RELATED APPLICATIONS

The instant application is a U.S. National Stage application of and claims priority to PCT/EP2020/059902, filed on Apr. 7, 2020, which is a PCT application of and claims priority to FR Application No. FR1903739, filed on Apr. 8, 2019, the subject matter of both aforementioned applications are hereby incorporated by reference in their entireties.

TECHNICAL FIELD

The invention relates to an apparatus for the collection of blood from a donor as well as a system for the collection of a target volume of blood.

BACKGROUND

It applies to the medical field, and in particular to apparatuses used for the collection and the mixing of blood during a sampling of blood.

Blood samples are usually taken using a system with bags comprising at least one collecting bag for the blood of the donor, connected via a flexible tube, to a collection needle. During the collection, the collection needle is inserted into the vein of a donor. The collecting bag comprises an anticoagulant of the acid-citrate-dextrose (ACD) or citrate-phosphate-dextrose (CPD) type in order to prevent the collected blood from coagulating.

According to the European standards, the volume of blood sampled must be comprised between 485 and 535 ml of blood, according to the sex, height and weight of the donor.

Automated apparatuses for collecting blood exist on the market. These apparatuses typically include an agitator plate on which the collecting bag of the blood rests and a device for clamping the flexible tube connecting the collecting bag and the sampling needle. The apparatus is programmed to clamp the flexible tube when the volume of blood to be sampled is reached so as to stop the sampling.

For the proper operation of the apparatuses, it is important that the volume of blood sampled be determined precisely and reliably.

The determination of the volume of blood sampled is generally carried out by detection of the weight of the bag during blood collection.

Document WO 2016/084001 describes an example of an automated blood collection apparatus that essentially comprises a plate intended for receiving a collecting bag for the blood, a unit for setting said plate into motion so as to mix the blood collected and the anticoagulant contained in said collecting bag, a detector configured to detect the weight of the collecting bag all throughout the sampling, and a clamping device for closing a flexible tube connected to said collecting bag, the clamping device being controlled to clamp said flexible tube at the end of the sampling, i.e. when the target volume is reached. In order to improve the precision of the weighing or of the measuring of the volume of blood collected, the agitation of the plate is stopped 25 to 30 ml before reaching the target volume of blood to be collected, in such a way as to be able to continuously determine the volume of blood collected until the target volume. This solution has the disadvantage of having to stop the agitation of the collecting bag at the approach of the end of the sampling, increasing the risk of clots forming.

In document WO 2017/216343, a collection apparatus is described that comprises a clamping device associated with a drive member which can be a stepper motor.

SUMMARY

The invention proposes an apparatus for collecting blood from a donor making it possible to collect a target volume of blood with precision.

To this effect and according to a first aspect, the invention proposes an apparatus for the collection of a target volume of blood in a collecting bag of a system with bags further comprising a collection needle connected to said collecting bag via a flexible tube, comprising:
- a plate intended for receiving the collecting bag,
- a clamping device of said flexible tube comprising (a) a bearing element having a bearing surface against which said flexible tube is intended for being clamped, (b) a clamping element having a clamping surface facing the bearing surface, said clamping element being able to move with respect to said bearing element between at least one open position according to which the flexible tube placed between the bearing surface and the clamping surface is not deformed and an obturation position according to which the flexible tube placed between the bearing surface and the clamping surface is obstructed, and (c) a control unit configured for
  determining the volume of blood collected in said collecting bag, and
  displacing the clamping element from the open position to a first intermediate position between said open position and the obturation position, when the determined volume of blood collected in said collecting bag reaches a predetermined volume.

According to another aspect, the invention relates to a system for the collection of a target volume of blood comprising on the one hand an apparatus according to the first aspect and on the other hand a system with bags comprising a collecting bag and a collection needle connected to said collecting bag via a flexible tube.

BRIEF DESCRIPTION OF THE DRAWINGS

Other objects and advantages shall appear in the following description.

The accompanying drawings illustrate the invention.

DETAILED DESCRIPTION

Figure 1:
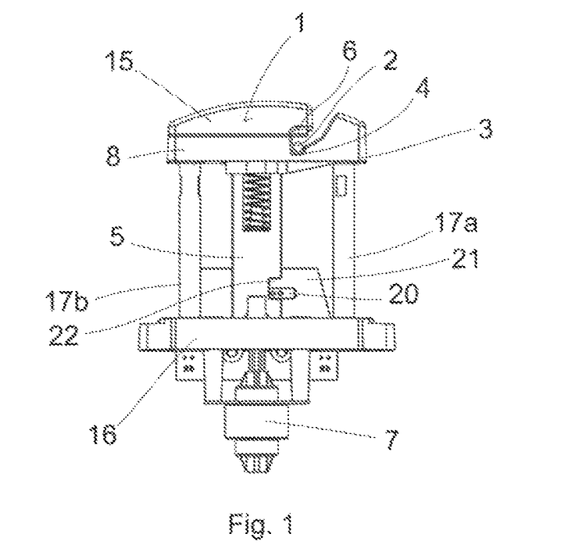
FIG. 1 shows a schematic front view of a clamping device according to an embodiment in a large open position.

The FIG. 1 shows a clamping device according to the first embodiment. This clamping device is provided to be part of a medical apparatus, in particular of an apparatus for collecting blood from a donor or from a patient. This clamping device 1 is intended for clamping a flexible tube 2 until the obturation of a passage section of said flexible tube and thus prevent the passage of a fluid through said section.

This clamping device comprises:
- a bearing element 3 comprising a bearing surface 4 against which a flexible tube 2 is intended for being clamped, and
- a clamping element 5 comprising a clamping surface 6 facing the bearing surface 4, said clamping element 5 being able to move with respect to said bearing element 3 between at least one open position, an obturation position and a closed position.

Figure 2:
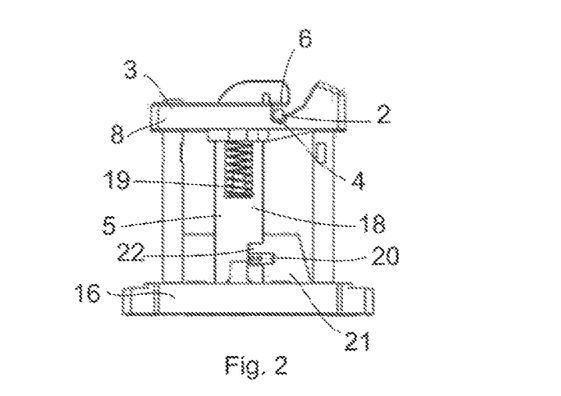
FIG. 2 shows a partial schematic view of the clamping device of FIG. 1 in a large open position.
Figure 3:
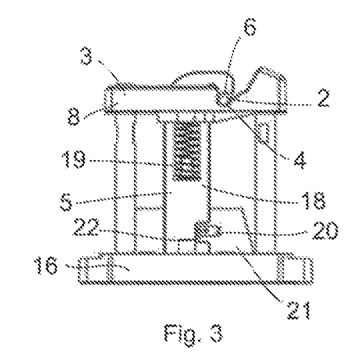
FIG. 3 shows a partial schematic view of the clamping device of FIG. 1 in a small open position.

The expression "open position" corresponds to the position according to which the flexible tube placed between the bearing surface and the clamping surface of the clamping device is not deformed. In this position, shown in FIGS. 1 to 3, the bearing surface 4 and the clamping surface 6 are separated from one another by a distance greater than or equal to the outer diameter of the flexible tube to be clamped.

When the distance between the bearing surface 4 and the clamping surface 6 is greater than the outer diameter D of the flexible tube 2 (FIG. 9), the open position is referred to as "large open position". This position, shown in FIGS. 1 and 2, allows for example an operator to insert the flexible tube 2 into the clamping device 1, between the bearing surface 4 and the clamping surface 6.

When the distance between the bearing surface 4 and the clamping surface 6 is substantially equal to the outer diameter D of the flexible tube 2, the open position will be referred to as "small open position". In this position, shown in FIG. 3, the flexible tube is maintained in place in the clamping device by an interference fit.

The expression "obturation position" corresponds to the position according to which the flexible tube 2 placed between the bearing surface 4 and the clamping surface 6 of the clamping device 1 is obstructed. In this obturation position, shown in FIG. 4, a section of passage of the flexible tube 2 is closed, preventing the passage of a fluid through this section. The distance between the bearing surface 4 and the clamping surface 6 substantially corresponds to twice the thickness of the wall of the flexible tube. In relation to FIG. 9, the thickness of the wall of a flexible tube 2 corresponds to the difference between the outer diameter D of the flexible tube and the inner diameter d of said flexible tube.

The expression "closed position" corresponds to the position according to which the bearing surface 4 and the clamping surface 6 of the clamping device 1 are in contact. In this closed position, shown in FIG. 5, the flexible tube is absent from the clamping device.

For example, for a flexible tube having an inner diameter d of 3.5 mm and an outer diameter D of 4.1 mm, the distance between the bearing surface 4 and the clamping surface 6 of the clamping device is substantially 6 mm in the large open position, 4 mm in the small open position, 1.2 mm in the obturation position, and 0 mm in the closed position.

The clamping device 1 further comprises a drive member 7 arranged to produce a movement and to transmit it to said clamping element 5. In a particular embodiment, the drive member 7 is configured to linearly displace the clamping element 5. Alternatively, the clamping element is movable in rotation.

For example, the drive member is a linear motor, particularly a linear stepper motor. Alternatively, the drive member is an electro-magnet motor, a DC or AC motor, a brushless motor, or a pneumatic or hydraulic cylinder.

According to a particular embodiment shown in FIGS. 6 to 9, the bearing element 3 comprises a first portion 8 with a housing 9 for said flexible tube. The housing 9 is in the form of a recess comprising a substantially flat bottom 10 formant a bearing surface 4, and two lateral walls 11a, 11b parallel together extending from said bottom 10. The width of the housing corresponds substantially to the outer diameter D of the flexible tube 2.

The first portion 8 of the bearing element 3 further comprises an opening 12 for the displacement of the clamping element described in more detail hereinbelow. This opening 12 is in particular in the form of a slot. The opening 12 is isolated from said housing 9 by one of said lateral walls 11b of the housing 9. Thus, in case of a leak of the fluid contained in the flexible tube 2 at the clamping device 1, the fluid flows in the housing 9 of the bearing element 3 but cannot pass inside the clamping device through the opening 12. The risk of the fluid flowing inside the clamping device 1 through the opening 12 provided for the clamping element 5 is therefore reduced.

Advantageously, the bottom 10 of the housing 9 has a slope, for example between 1 and 5 degrees, in relation to the horizontal, so as to direct the fluid that can flow from the flexible tube to the outside of the clamping device and/or to the outside of the apparatus comprising said clamping device. For example, in FIG. 11, the bottom of the slope is on the side opposite the agitator plate 26 of the collection apparatus 23.

Figure 8:
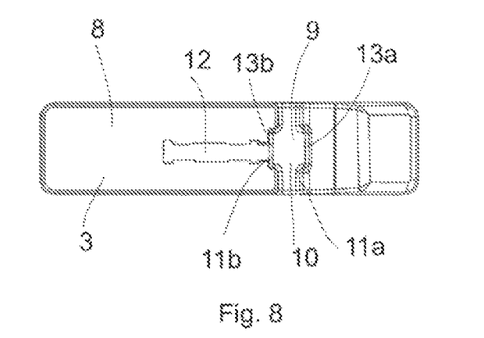
FIG. 8 shows a schematic top view of the bearing element of the clamping device of FIG. 1

According to FIG. 8, the housing 9 of said flexible tube further comprises a notch 13a, 13b on each one of said lateral walls 11a, 11b allowing for the crushing of the flexible tube by the clamping element.

Figure 9:
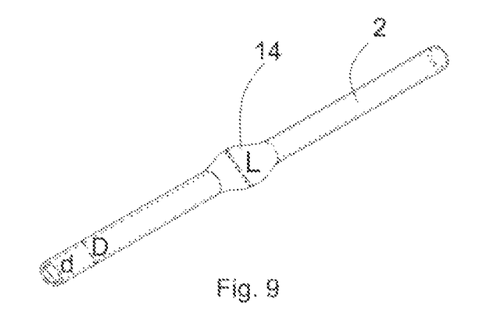
FIG. 9 shows a schematic view and in perspective of a clamped flexible tube.

Indeed, as shown in FIG. 9, when a flexible tube is crushed, the crushing zone 14 has a width L greater than the outer diameter D of the flexible tube.

According to a particular embodiment and in relation to FIG. 1, the bearing element 3 further comprises a cover 15 intended for being mounted above the first portion 8 of the clamping device 1. This cover 15 protects the clamping element 5 when it is mounted in the bearing element 3 so as to prevent an operator from hindering the movement of the clamping element during the operation of the clamping device.

The bearing element 3 comprises a second portion 16 engaged with the first portion 8 via two rigid rods 17a, 17b.

In FIG. 1, the drive member 7 of the clamping element 5 is fastened to the second portion 16. The clamping element 5 is engaged with the drive member 7. The clamping element 5 is arranged between the first and the second portion 8, 16 of the bearing element 3.

The clamping element 5 is linearly mobile through the opening 12 of the bearing element 3.

Figure 6:
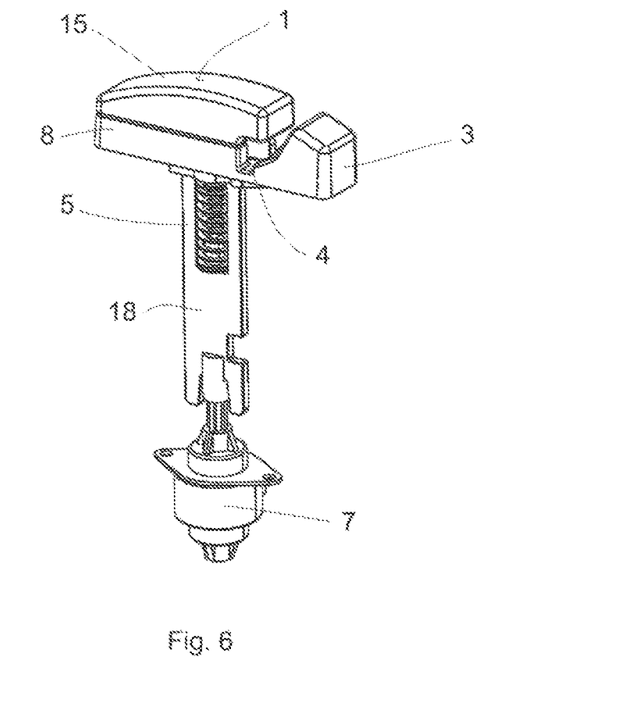
FIG. 6 shows a partial schematic view and in perspective of the clamping device of FIG. 1.
Figure 7:
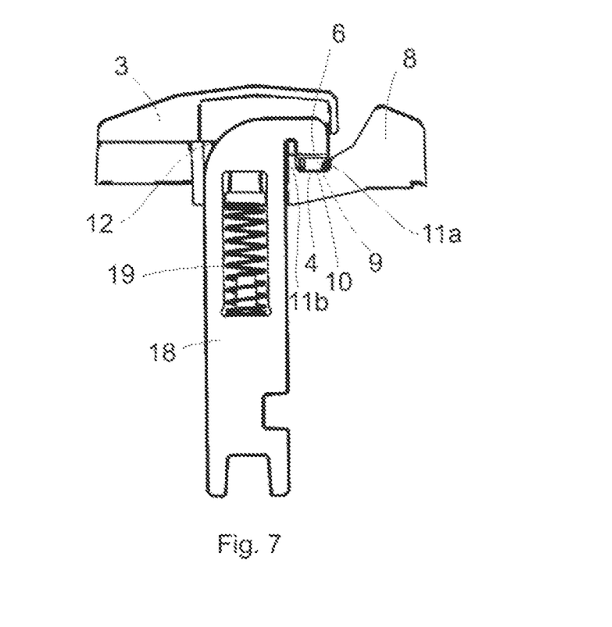
FIG. 7 shows a partial schematic and cross-section view of the clamping device of FIG. 1.

According to FIGS. 6 and 7, the clamping element 5 comprises a body 18 in the form of a plate coupled at one end to the drive member 7 and comprising at the other end a curved portion ending with the clamping surface 6.

As shown in FIG. 7, the clamping element 5 substantially has the shape of a cross or of an inverted letter J. This particular shape contributes to the seal of the clamping device 1. Indeed, during the displacement of the clamping element 5, the clamping surface 6 is displaced towards the bearing surface 4 along an axis that is distinct from the axis wherein the plate forming the body 18 is displaced. The opening 12 of the bearing element 3, through which the plate forming the body of the clamping element 5 is displaced, is isolated from the clamping surface 6 and from the bearing surface 4. In case of leakage of a liquid contain in the flexible tube, the liquid cannot pass through the opening 12 of the bearing element and therefore does not penetrate inside the clamping device 1.

The clamping element 5 advantageously comprises a spring 19 arranged in the initial position, to place the clamping element 5 in the closed position. In FIG. 7, the spring is disposed in an opening of the plate forming the body 18 of the clamping element and abuts against the first portion 8 of the bearing element 3.

The drive member 7 is in particular a stepper motor linear actuator of an anti-rotation system such as described in document U.S. Pat. No. 7,969,048.

As shown in FIGS. 1 to 5, the clamping device 1 advantageously comprises a position detector 20 intended for determining the position of the clamping element 5, and in particular the obturation position and the closed position.

This position detector 20 is separated from the bearing surface 4 and from the clamping surface 6 of the clamping device 1, i.e. it is not at the flexible tube 2 to be clamped. The position detector 20 indirectly detects the position of the clamping element 5 in relation to a the bearing element 3.

In particular, the position detector 20 is a sensor comprising a transmitter of a signal and a receiver of the signal transmitted. This sensor engages with the clamping element 5 to detect the position of said clamping element. This sensor is in particular a contactless sensor of the optical, inductive, capacitive, magnetic or ultrasonic type.

In a particular configuration, the position detector 20 comprises an optical sensor. The sensor cooperates with the bearing element 3. As shown in FIG. 1, the sensor forming the position detector 20 is in particular fastened onto a panel 21 integral with the second portion 16 of the bearing element 3.

According to FIGS. 1 to 5, the clamping element 5 comprises an opening 22 that engages with the sensor in such a way as to authorise the receiving by the receiver of the signal transmitted by the transmitter when the clamping element is in one of the obturation or closed positions and in such a way as to prevent the receiver from receiving the signal transmitted by the transmitter when the clamping element is in the other position.

For example, the signal is an optical signal of the light beam type. The transmitter and the receiver of the optical sensor are arranged on the same side of the plate 21 of the clamping element 5. In the closed position (FIG. 5), the transmitter and the receiver of the optical sensor are facing the solid portion of the plate and the light emitted by the transmitter is received by the receiver. In the obturation position (FIG. 4), the transmitter and the receiver are both facing the opening, and the light transmitted is not received by the receiver.

In particular, the opening is arranged to prevent the reception of the signal by the receiver in the large and small open position.

Alternatively, the opening of the clamping element is arranged to partially authorise the reception of the signal by the receiver in the obturation position and to prevent the reception of the signal in the open positions.

Figure 10:
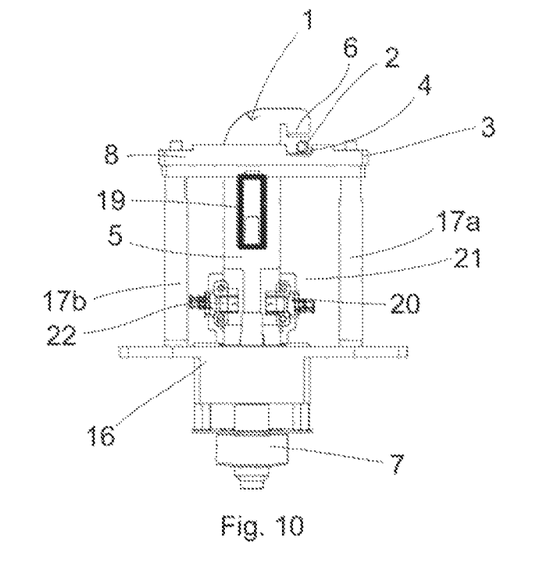
FIG. 10 shows a schematic view of a clamping device according to another embodiment.

According to an alternative embodiment shown in FIG. 10, the clamping device 1 is designed to determine the four positions of the clamping element 5, namely the large open, small open, obturation and closed position.

In this embodiment, the position detector 20 comprises a pair of sensors, that engage with at least one pair of openings 22 in the clamping element 5. This pair of sensors and openings make it possible to determine the position of the clamping element using a truth table.

An example of a truth table is as follows, wherein 1 corresponds to the transmission of the light to the receiver of the optical sensor and 0 corresponds to the absence of transmission of the light to the optical sensor.

TABLE 1

| Position | Sensor 1 | Sensor 2 |
| --- | --- | --- |
| Large open | 1 | 0 |
| Small open | 0 | 0 |
| Obturation | 1 | 1 |
| Closed | 0 | 1 |

The clamping device 1 further comprises a control unit that controls the displacement of the clamping element 5.

The control unit has the form of an electronic and computerised system that comprises for example a microprocessor designed to execute a program of commands. The execution of this program allows the control unit to control in particular the clamping device, according for example to the signals received by the position detector.

In this case and advantageously, in order to detect the presence or the absence of a flexible tube 2 in the clamping device 1, the control unit is configured for:
  actuating the clamping element 5 from the open position towards the closed position until the clamping element 5 is blocked,
  detecting the position of the clamping element thus blocked, and
  determining the presence or the absence of the flexible tube according to the position of the clamping element detected.

The blocking of the clamping element 5 is produced when the clamping element 5 is stopped in its displacement, either by the presence of the flexible tube 2 crushed between the bearing surface 4 and the clamping surface 6, or by the bearing surface 4 directly.

Figure 4:
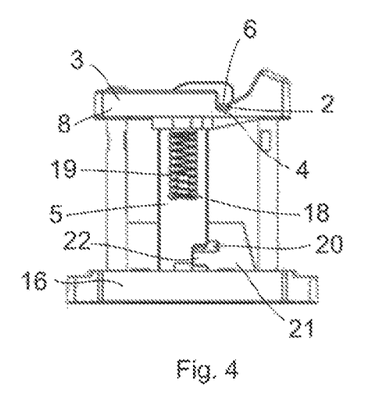
FIG. 4 shows a partial schematic view of the clamping device of FIG. 1 in an obturation position.
Figure 5:
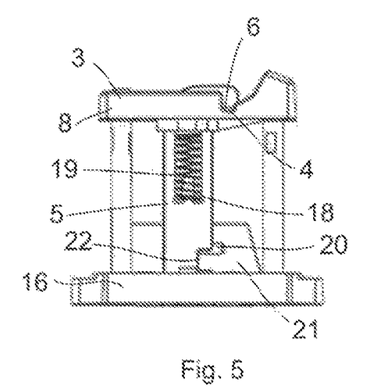
FIG. 5 shows a partial schematic view of the clamping device of FIG. 1 in a closed position.

In particular, the presence of a flexible tube 2 is determined if the position of the clamping element detected is the obturation position (FIG. 4). The absence of a tube is determined if the position of the clamping element 5 detected is the closed position (FIG. 5).

The control unit is configured to react differently according to the presence or the absence of a flexible tube.

For example, if the flexible tube is absent from the clamping device, the control unit is configured to emit an audible and/or visual alert signal intended for the operator in order to alert them to the absence of a tube. In addition or alternatively, the control unit is configured to stop the apparatus comprising the clamping device.

If the flexible tube is present in the clamping device, the control unit is configured to continue the operation of the apparatus.

According to an advantageous embodiment, the control unit is furthermore configured to verify, prior to the operations for detecting the flexible tube, for example at the starting of the apparatus comprising the clamping device, that the different positions of the clamping element are correctly detected. This control operation makes it possible to ensure that during later detections, the cases of failure do not induce incorrect reactions of the control unit.

For example, prior to the operations for detecting the flexible tube and in the absence of a flexible tube in the clamping device, the control unit is configured, for:
- actuating the clamping element 5 from the open position towards the closed position until the clamping element is blocked
- detecting the position of the clamping element 5 thus blocked,
- determining the correct operation of the clamping device 1 according to the position of the clamping element 5 detected.

If the position of the clamping element detected is the closed position, the device is operating correctly. If the position of the clamping element detected is not the closed position, the clamping device is defective. An alert signal can be emitted for the attention of the operator.

The clamping device 1 described hereinabove with a flexible tube 2 forms a system for determining the presence or the absence of a flexible tube in a clamping device.

A method for detecting a flexible tube 2 in a clamping device 1 shall now be described, said method comprising the operations of:
- actuating the clamping element 5 from the open position towards the closed position until the clamping element 5 is blocked,
- detecting the position of the clamping element 5 thus blocked,
- determining the presence or the absence of the flexible tube 2 according to the position of the clamping element 5 detected.

The presence of a flexible tube is determined if the position of the clamping element detected is the obturation position; the absence of a flexible tube is determined if the position of the clamping element detected is the closed position.

The clamping device such as described hereinabove is generally comprised in an apparatus.

Such an apparatus is in particular an apparatus for medical use which can be an infusion pump, a flexible tube welding machine, a device for clamping and welding flexible tubes or an apparatus for treating blood. In a particular example, the apparatus is an apparatus for the collection of blood.

Figure 11:
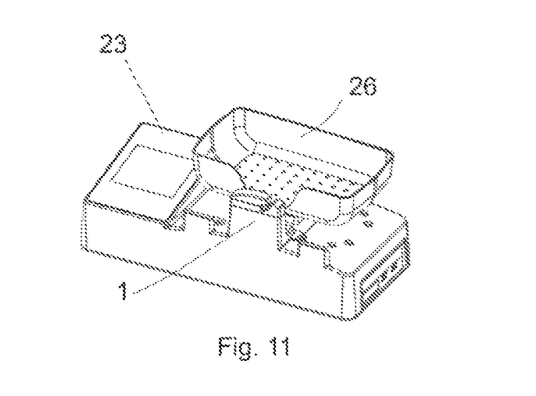
FIG. 11 shows a schematic view of a medical apparatus comprising a clamping device of FIG. 1.
Figure 12:
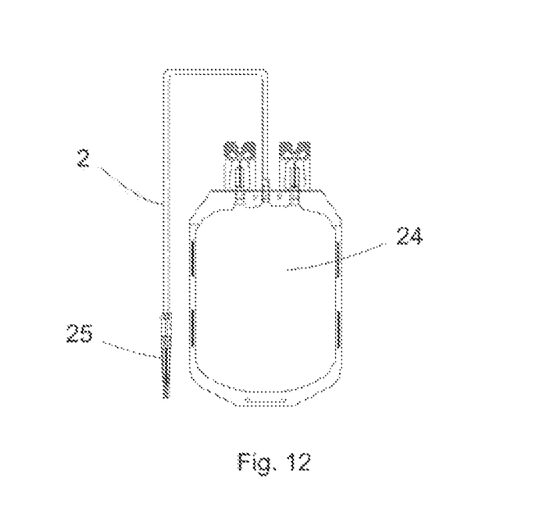
FIG. 12 shows a schematic view of a system with bags that can be used with the apparatus of FIG. 11.

Such an apparatus 23 for collecting blood is shown in FIG. 11 and an example of a system with bags for collecting blood is shown in FIG. 12.

The system with bags comprises at least one collecting bag 24 to collect the blood, said collecting bag being connected to a collection needle 25 via a flexible tube 2. The collecting bag 24 advantageously contains an anticoagulant solution. The collection needle is intended for being introduced into the vein of a donor in order to collect their blood in the collecting bag.

A system for the collection of a target volume of blood comprising on the one hand an apparatus for the collection of a target volume of the blood and on the other hand a system with bags comprising a collecting bag 24 and a collection needle 25 connected to said collecting bag via a flexible tube, is described hereinafter in more detail.

The apparatus for the collection of a target volume of blood in a collecting bag of a system with bags further comprising a collection needle 25 connected to said collecting bag via a flexible tube 2, comprises a plate 26 intended for receiving the collecting bag 24.

Advantageously, the apparatus further comprises an agitation device to set the plate in motion in order to agitate the collecting bag. The agitation of the collecting bag contributes to mixing the blood collected and the anticoagulant solution contained in the collecting bag 24.

A particular method for collecting a target volume of blood in a collecting bag 24 of a system with bags further comprising a collection needle 25 connected to said collecting bag via a flexible tube 2, comprises the following steps:
- determining the volume of blood collected in said collecting bag 24, and
- partial clamping of the flexible tube so as to reduce the flow rate of the blood collected, when the determined volume of blood collected in said collecting bag 24 reaches a predetermined volume.

After the step of partial clamping of the flexible tube, the method comprises in particular the step of obturating the flexible tube upon reaching the target volume of blood to be collected so as to stop the collection of blood.

To in particular implement this method, the apparatus for the collection comprises, in addition to the plate 26 intended for receiving the collecting bag, a clamping device 1 of a flexible tube such as described hereinabove and essentially comprising:
(a) a bearing element 3 having a bearing surface 4 against which said flexible tube 2 is intended for being clamped,
(b) a clamping element 5 having a clamping surface 6 facing the bearing surface 4, said clamping element 5 being able to move with respect to said bearing element 3 between at least one open position according to which the flexible tube placed between the bearing surface 4 and the clamping surface 6 is not deformed and an obturation position according to which the flexible tube placed between the bearing surface 4 and the clamping surface 6 is obstructed, and
(c) a control unit configured for
- determining the volume of blood collected in said collecting bag 24, and
- displacing the clamping element 5 from the open position to a first intermediate position between said open position and the obturation position, when the determined volume of blood collected in said collecting bag reaches a predetermined volume.

The displacement of the clamping element until a first intermediate position partially clamps the flexible tube by reducing the section of passage of said flexible tube.

This partial clamping of the flexible tube has for effect to reduce the flow rate of blood collected. This reduction in the flow rate at the end of the blood collection procedure makes it possible to reach the target volume of blood to be collected with more precision, without excessively prolonging the collection time since the reduction in the flow rate is implemented only when approaching the end of the collection procedure.

In particular, the predetermined volume of blood collected from which the flow rate is reduced, is comprised within the range from 90 to 99% of the target volume of blood to be collected, more particularly in the range from 95 to 99% of the target volume of blood to be collected. This predetermination is carried out by the control device before the beginning of the collection of the fluid.

For example, for a target volume of 450 ml of fluid to be collected, the flow rate in the flexible tube is reduced when the volume of fluid collected reaches 440 ml.

The intermediate position is set by the control unit. It can be predetermined before the collection of the blood, for example according to the target volume of blood to be collected or set during the collection of the blood, for example according to the actual flow rate of the blood collected.

For example, the first intermediate position substantially corresponds to the median position between the small open position and the obturation position.

Alternatively, the control unit is configured for, after the displacement of the clamping element 5 to the first intermediate position, displacing the clamping element from the first intermediate position to a second intermediate position between said first intermediate position and the obturation position, when the determined volume of blood collected in the collecting bag reaches another predetermined volume of collected blood.

This operation makes it possible to further reduce the flow rate of the collected blood at the approach of the target volume of blood to be collected.

The displacement of the clamping element in its different positions is implemented by the use of a drive member 7 in the form of a stepper motor, which according to the type of motor, allows for a displacement precision of about 0.013 mm.

In order to determine the volume of blood collected in the collecting bag, the collection apparatus further comprises a device for measuring the volume of blood collected. In particular, this device is a weighing device associated with the plate for measuring the weight of the collecting bag. The volume of blood collected in the collecting bag is then deducted from the weight of the collecting bag containing the collected blood.

When the collection apparatus is turned on, the control unit is configured to place the clamping element 1 in a large open position so as to allow the operator to place the flexible tube 2 in said clamping device 1. The operator furthermore places the collecting bag 24 and the rest of the system with bags on the plate 26.

The control unit is then configured to displace the clamping element 5 from the large open position to the obturation position. When the flexible tube is obstructed, the operator inserts the needle into a vein of the donor.

Then, the control unit is configured to displace the clamping element from the obturation position to the small open position so as to allow for the collection of the blood from the donor by maintaining the flexible tube 2 in the clamping device 1.

Advantageously, immediately after the displacement of the clamping element in a large open position, the control unit is configured to implement the operations described hereinabove making it possible to determine the presence or the absence of the flexible tube 2 in the clamping device 1. The displacement of the clamping element 5 in a small open position in order to allow for the collection of blood is then authorised only if the flexible tube is present in the clamping device.

In this case, the clamping device further comprises a position detector 20 configured for detecting the position of the clamping element 5, in particular the obturation position and the closed position.

In case of absence of a flexible tube, the control unit is configured to alert the operator as to the absence of a tube. In case of presence of a flexible tube, the control unit is configured to start the collection procedure of the blood, in particular by displacing the clamping element 5 in the small open position.

When the target volume of blood is collected in the collecting bag 24, the control unit is configured to displace the clamping element 5 from the small open position to the obturation position when the target volume of blood is reached, in order to stop the collection of the blood.

What is claimed is:

1. An apparatus for collecting a target volume of blood in a collecting bag of a bag system further comprising a collection needle connected to the collecting bag via a flexible tube, said apparatus comprising:
   a plate intended for receiving the collecting bag,
   a clamping device of the flexible tube comprising a bearing element having a bearing surface against which said flexible tube is intended for being clamped, a clamping element having a clamping surface facing the bearing surface, the clamping element configured to move with respect to the bearing element between at least one open position where the flexible tube placed between the bearing surface and the clamping surface is not deformed and an obturation position where the flexible tube placed between the bearing surface and the clamping surface is obstructed; and
   a control unit, configured for determining the volume of blood collected in said collecting bag and displacing the clamping element from the open position to a first intermediate position between the open position and the obturation position, when the determined volume of blood collected in the collecting bag reaches a predetermined volume.

2. The apparatus according to claim 1, wherein said predetermined volume is comprised within a range from 90 to 99% of the target volume of blood to be collected.

3. The apparatus according to claim 1, wherein said first intermediate position corresponds to the median position between a small open position according to which the distance between the bearing surface and the clamping surface is equal to the outer diameter D of the flexible tube, and the obturation position.

4. The apparatus according to claim 3, wherein the control unit is configured to displace the clamping element from the small open position to the obturation position when the target volume of blood is reached.

5. The apparatus according to claim 1, wherein the control unit is further configured for, after the displacement of the clamping element to the first intermediate position, displacing the clamping element from the first intermediate position to a second intermediate position between said first intermediate position and the obturation position, when the determined volume of blood collected in the collecting bag reaches a second predetermined volume.

6. The apparatus according claim 1, wherein the clamping device further comprises a drive member configured to linearly displace the clamping element.

7. The apparatus according to claim 6, wherein the drive member is a stepper motor.

8. The apparatus according to claim 1, wherein clamping device further comprises a position detector configured for detecting a position of the clamping element.

9. The apparatus according to claim 1 further comprising an agitation device for setting the plate into motion.

10. The apparatus according to claim 1 further comprising a weighing device associated with the plate for determining the weight of the collecting bag.

11. A system for collecting a target volume of blood comprising the apparatus according to claim 1 and a collecting bag and a collection needle connected to the collecting bag via a flexible tube.

* * * * *